United States Patent
Furukawa et al.

(10) Patent No.: US 9,943,231 B2
(45) Date of Patent: Apr. 17, 2018

(54) APPARATUS AND METHOD FOR OBTAINING SUBJECT INFORMATION, DISPLAY METHOD, AND PROGRAM

(71) Applicant: CANON KABUSHIKI KAISHA, Tokyo (JP)

(72) Inventors: Yukio Furukawa, Kyoto (JP); Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 607 days.

(21) Appl. No.: 14/527,579

(22) Filed: Oct. 29, 2014

(65) Prior Publication Data
US 2015/0119684 A1 Apr. 30, 2015

(30) Foreign Application Priority Data
Oct. 31, 2013 (JP) .................................. 2013-227235

(51) Int. Cl.
*A61B 5/00* (2006.01)
(52) U.S. Cl.
CPC ............ *A61B 5/0095* (2013.01); *A61B 5/004* (2013.01); *A61B 5/4312* (2013.01); *A61B 5/7203* (2013.01)
(58) Field of Classification Search
CPC ..... A61B 5/4312; A61B 5/004; A61B 5/7203; A61B 5/0095; A61B 8/5269; A61B 8/5215; A61B 8/5207
See application file for complete search history.

(56) References Cited

U.S. PATENT DOCUMENTS

| 5,357,962 A | * | 10/1994 | Green | G10K 11/346 600/443 |
| 5,713,356 A | | 2/1998 | Kruger | |
| 6,102,857 A | * | 8/2000 | Kruger | A61B 5/0091 600/425 |
| 6,292,682 B1 | * | 9/2001 | Kruger | A61B 5/0091 600/407 |
| 8,784,318 B1 | * | 7/2014 | Napolitano | G01S 7/52049 600/443 |
| 2002/0035327 A1 | * | 3/2002 | Kruger | A61B 5/0091 600/437 |

(Continued)

FOREIGN PATENT DOCUMENTS

WO 2010/030817 A1 3/2010

OTHER PUBLICATIONS

Treeby et al. "Automatic sound speed selectio in photoacoustic image reconstruction using an autofocus approach." J Biomedical Optics. (Sep. 2011) vol. 16(9), 3 pages.*

(Continued)

*Primary Examiner* — Long V Le
*Assistant Examiner* — Angela M Hoffa
(74) *Attorney, Agent, or Firm* — Canon USA, Inc. I.P. Division

(57) ABSTRACT

A subject-information acquisition apparatus includes a light source; a holding member configured to hold a subject so as to surround the subject; at least one transducer configured to receive an acoustic wave generated by irradiating the subject with light from the light source; and a signal processing unit configured to obtain distribution information using a received signal output from the transducer. The holding member includes a marker that absorbs the light and generates an acoustic wave.

13 Claims, 11 Drawing Sheets

(56) References Cited

U.S. PATENT DOCUMENTS

| | | | | |
|---|---|---|---|---|
| 2009/0227870 A1* | 9/2009 | Kolkman | | A61B 5/0095 600/447 |
| 2011/0232385 A1* | 9/2011 | Nanaumi | | A61B 5/0095 73/602 |
| 2011/0306865 A1* | 12/2011 | Thornton | | A61B 5/0059 600/407 |
| 2012/0190963 A1* | 7/2012 | Fukutani | | A61B 5/0091 600/407 |
| 2013/0123604 A1* | 5/2013 | Oyama | | A61B 5/0095 600/407 |
| 2013/0205903 A1* | 8/2013 | Oyama | | A61B 5/0095 73/596 |
| 2013/0217995 A1* | 8/2013 | Kruger | | A61B 5/6835 600/407 |
| 2013/0312526 A1 | 11/2013 | Oishi | | |
| 2014/0114172 A1* | 4/2014 | Abe | | A61B 5/0095 600/407 |
| 2014/0163353 A1* | 6/2014 | Razansky | | A61B 5/0095 600/407 |
| 2014/0235993 A1* | 8/2014 | Fukutani | | A61B 5/0095 600/407 |
| 2014/0296690 A1* | 10/2014 | Miyasato | | A61B 5/0095 600/407 |
| 2014/0316240 A1* | 10/2014 | Nagao | | A61B 8/463 600/407 |
| 2014/0360271 A1* | 12/2014 | Fukutani | | G01N 29/0654 73/602 |
| 2015/0031990 A1* | 1/2015 | Boctor | | A61B 34/20 600/424 |
| 2015/0114125 A1* | 4/2015 | Tanaka | | A61B 5/0095 73/632 |
| 2015/0119683 A1* | 4/2015 | Kyono | | A61B 5/704 600/407 |
| 2015/0238090 A1* | 8/2015 | Suita | | A61B 5/708 600/323 |
| 2015/0245771 A1* | 9/2015 | Wang | | A61B 5/0095 600/411 |
| 2016/0192843 A1* | 7/2016 | Kruger | | A61B 5/0095 600/407 |

OTHER PUBLICATIONS

Yoon et al. "Enhancement of photoacoustic image quality by sound speed correction: ex vivo evaluation". Optics Express. (Jan. 25, 2012) vol. 20(3), pp. 3082-3090.*

Jose et al. "Speed-of-sound compensated photoacoustic tomography for accurate imaging". Med Phys (Dec. 2012) 39)12), pp. 7262-7271.*

Resink et al. "Multiple passive element enriched photoacoustic computed tomography." Optics Letters (Aug. 1, 2011) vol. 36(5), pp. 2809-2811.*

* cited by examiner

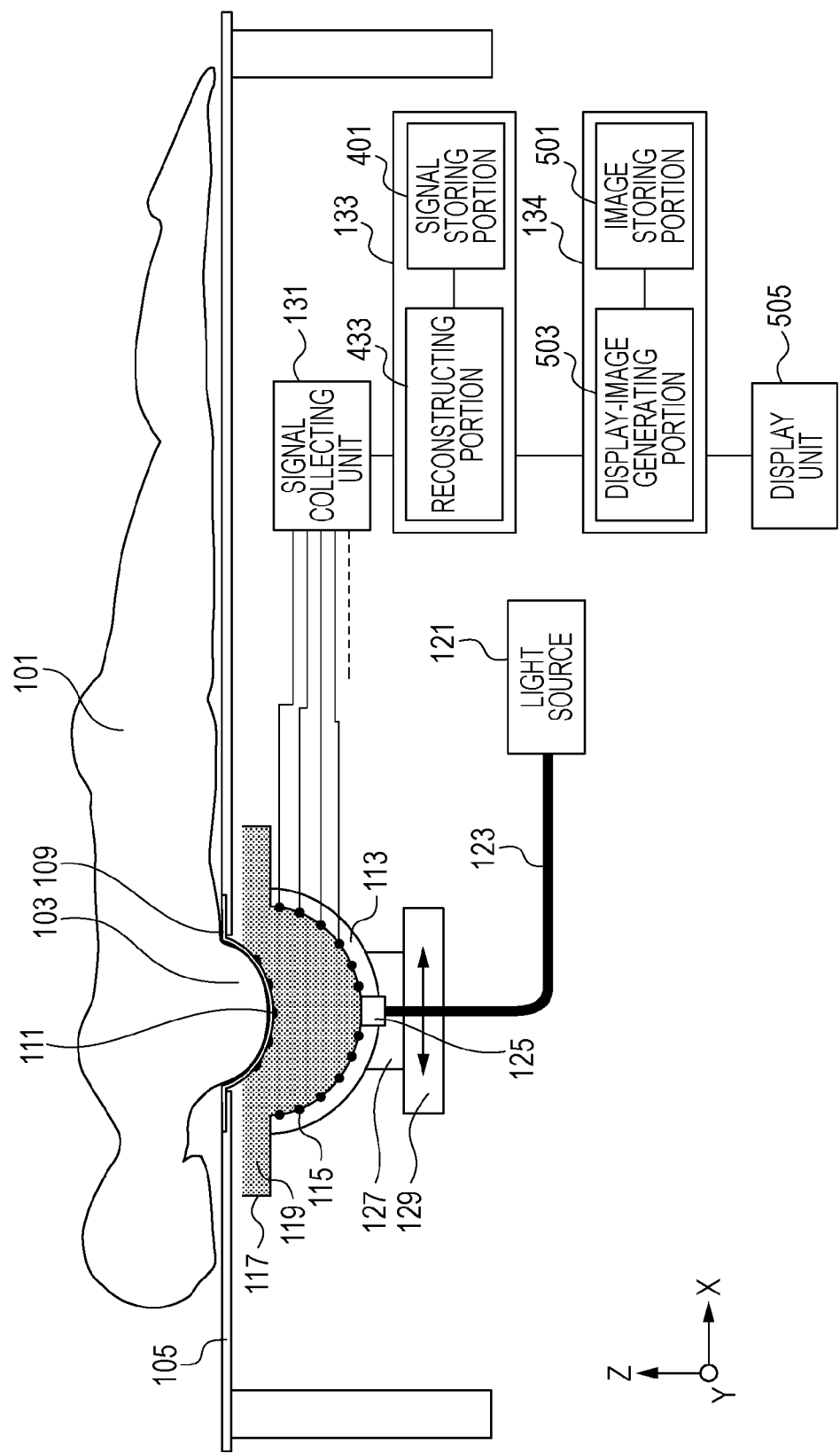

FIG. 5A
FIG. 5B
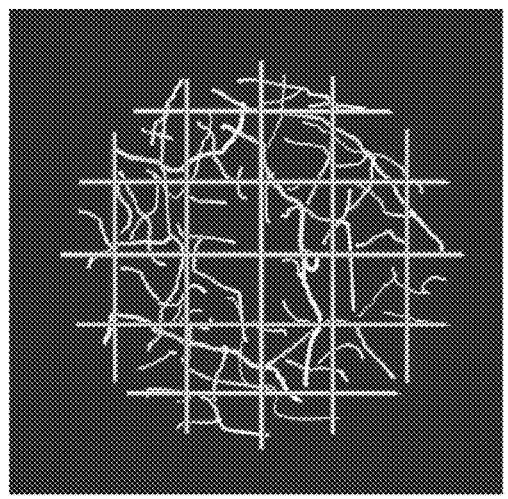
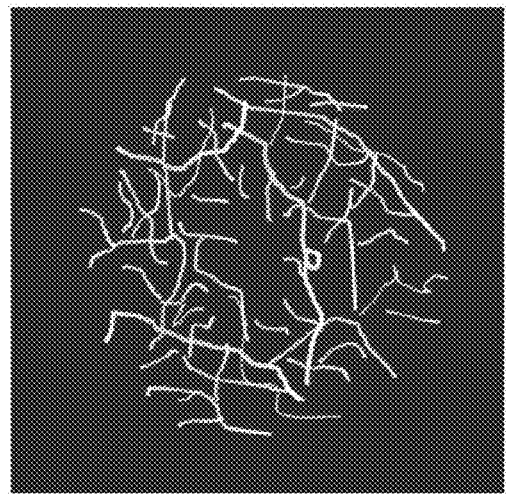

APEX   CENTER   BREAST WALL

603

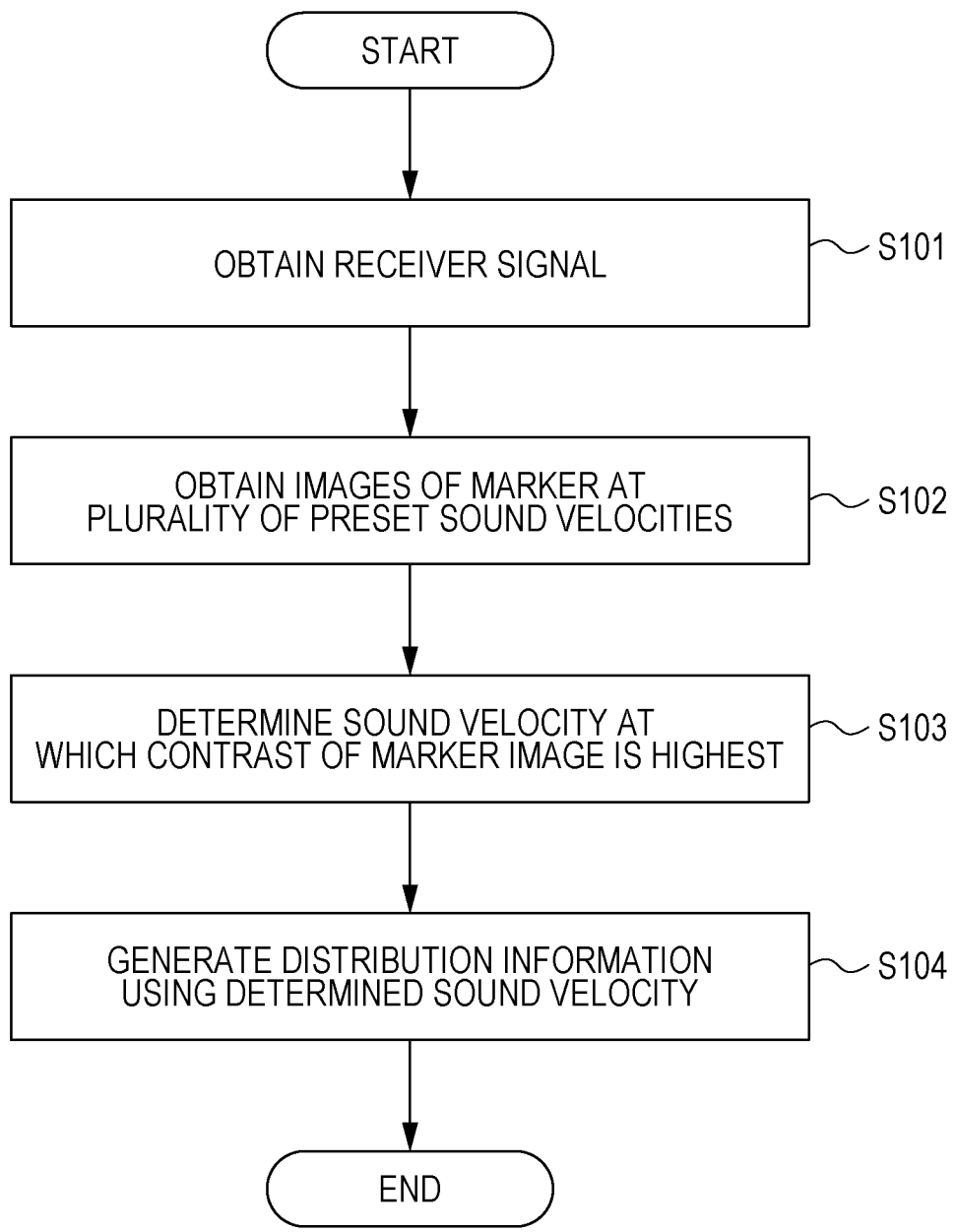

APPARATUS AND METHOD FOR OBTAINING SUBJECT INFORMATION, DISPLAY METHOD, AND PROGRAM

BACKGROUND OF THE INVENTION

Field of the Invention

The present invention relates to an apparatus and a method for obtaining subject information, a display method, and a program for the same. In particular, the present invention relates to a technique using acoustic waves generated by light irradiation.

Description of the Related Art

There is a photoacoustic imaging (PAI) technique for imaging tissue in a subject using a photoacoustic effect that, when the subject is irradiated with pulsed light generated from a light source, acoustic waves are generated in the subject due to absorption of the pulsed light.

International Publication No. WO/2010/030817 discloses an apparatus with a configuration in which a plurality of transducers that receive acoustic waves generated in a subject are disposed on a hemispherical supporting member. In examination, the subject is held by a thin cup-shaped holding member. Between the holding member and the transducers, an acoustic medium, such as water, through which acoustic waves can propagate is provided. Light is radiated from below a supporting member onto the subject through the holding member and the acoustic medium. Acoustic waves generated in the subject reach the transducers through the holding member and the acoustic medium.

Apparatuses including a holding member that holds a subject so as to surround the subject, as disclosed in International Publication No. WO/2010/030817, have an advantage in the viewpoint of usability that a load exerted on a person to be examined (hereinafter also referred to as an examinee) is low. On the other hand, an image presented to an examiner needs further improvement.

SUMMARY OF THE INVENTION

A subject-information acquisition apparatus according to a first aspect of the present invention includes a light source; a holding member configured to hold a subject so as to surround the subject; at least one transducer configured to receive an acoustic wave generated by irradiating the subject with light from the light source; and a signal processing unit configured to obtain distribution information using a received signal output from the transducer. The holding member includes a marker that absorbs the light and generates an acoustic wave.

A method for displaying an image on a display unit according to a second aspect of the present invention includes the steps of generating distribution information using a received signal caused by acoustic waves generated from a subject irradiated with light and a received signal caused by acoustic waves generated from a marker irradiated with light, the marker being provided on a holding member that holds the subject; and displaying the distribution information.

A method for obtaining subject information according to a third aspect of the present invention includes the steps of setting a sound velocity in an acoustic medium between a holding member that holds a subject and a transducer using a received signal caused by an acoustic wave generated from a marker irradiated with light, the marker being provided on the holding member; and generating the distribution information using a received signal caused by an acoustic wave generated from the subject irradiated with light and information on the sound velocity.

Further features of the present invention will become apparent from the following description of exemplary embodiments with reference to the attached drawings.

BRIEF DESCRIPTION OF THE DRAWINGS

FIG. 1 is a schematic diagram illustrating the configuration of a subject-information acquisition apparatus of a first embodiment.

FIG. 5A is a schematic diagram illustrating first distribution information.

FIG. 5B is a schematic diagram illustrating second distribution information.

FIG. 11 is a flowchart for explaining the processes of Example 8.

DESCRIPTION OF THE EMBODIMENTS

Figure 2A:
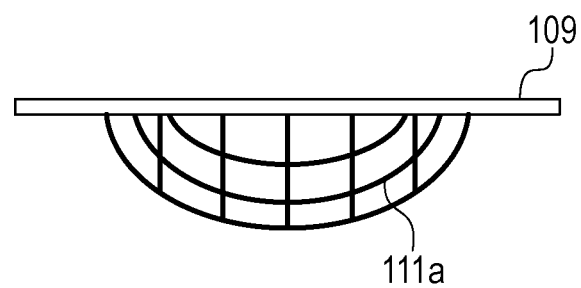
FIG. 2A is a schematic side view of a holding member.

Embodiments of the present invention will be described with reference to the drawings. Like components are denoted by the same reference signs, and descriptions thereof are omitted.

A subject-information acquisition apparatus according to an embodiment of the present invention obtains characteristic information indicating characteristic values corresponding to an individual plurality of positions in a subject using signals obtained by receiving acoustic waves. The acquired characteristic information reflects the absorptivity of light energy. Specific examples of the characteristic information include characteristic information that reflects the initial sound pressure of the generated acoustic waves, a light energy absorption density derived from the initial sound pressure, absorption coefficient, and the concentrations of constituents of the tissue. Examples of the concentrations of constituents include oxygen saturation, total hemoglobin concentration, and oxyhemoglobin or deoxyhemoglobin concentration. Two- or three-dimensional distribution information may be generated from characteristic information on a plurality of positions. The distribution information may be generated in the form of image data.

The subject-information acquisition apparatuses according to the following embodiments are mainly used for diagnoses of malignant tumors or blood diseases of humans and animals and observation of the progress of chemical treatment. Thus, supposed subjects include part of living organisms, specifically, objects to be examined, such as the breasts of humans and animals.

First Embodiment

The configuration and process of a subject-information acquisition apparatus of a first embodiment will be described.
Overall Apparatus Configuration
FIG. 1 is a schematic diagram illustrating the configuration of the subject-information acquisition apparatus of the first embodiment. The subject-information acquisition apparatus of this embodiment includes at least a light source 121, a plurality of transducers 115 that receive acoustic waves, a holding member 109 that holds a subject 103, and a signal processing unit 133 that obtains characteristic information on the interior of the subject 103 using received signals from the transducers 115.

Light from the light source 121 is transmitted through a light transmitting portion 123 and exits from a light emitting portion 125. The exiting light irradiates the subject 103 portion through acoustic matching liquid (acoustic medium) 119 and the holding member 109. Acoustic waves generated at a plurality of positions in the subject 103 by the irradiation of light reach the plurality of transducers 115 through the holding member 109 and the acoustic matching liquid 119.

The plurality of transducers 115 individually receive acoustic waves and output time-series received signals. The received signals are input to a signal collecting unit 131. The signal processing unit 133 generates distribution information including characteristic information on the interior of the subject 103 using signals output from the signal collecting unit 131.
Light Source 121
The light source 121 may be a pulsed light source capable of generating pulsed light of the order of nanoseconds to microseconds. Specifically, a pulse width of the order of 1 to 100 nanoseconds is set to efficiently generate acoustic waves. A preferable wavelength is from 600 nm to 1,100 nm. Specific examples of the light source 121 may be pulse lasers, such as an Nd:YAG laser and an alexandrite laser. Other examples are a Ti:sa laser and an OPO laser that uses Nd:YAG laser beam as exciting light. In addition, a semiconductor laser may be used. The light from the light source 121 is transmitted to the light emitting portion 125 through the light transmitting portion 123. The light transmitting portion 123 may be an optical system, such as a lens, a mirror, or an optical fiber. The light emitting portion 125 may be an optical system, such as a diffuser or a lens. The light emitting portion 125 is integrated with a supporting member 113.
Supporting Member 113
The supporting member 113 is a member that fixedly supports the plurality of transducers 115. As shown in FIG. 1, the supporting member 113 has a bowl-shaped portion having a spherical surface. Receiving portions of the plurality of transducers 115 are disposed at the inner wall of the bowl-shaped portion. The supporting member 113 has a frame portion 117 larger than the diameter of the bowl-shaped portion at the subject side with respect to the bowl-shaped portion. For examination, the bowl-shaped portion and the frame portion 117 are filled with the acoustic matching liquid 119 serving as an acoustic medium. The acoustic matching liquid 119 is composed of a material having an acoustic impedance close to that of human bodies to cause little attenuation of acoustic waves. For example, the acoustic matching liquid 119 preferably has an impedance of 1.3 MRayls or higher and 2 MRayls or lower. Specific examples include water and oil.

The supporting member 113 is disposed on a stage 127. A moving mechanism 129 can move the supporting member 113 in an X-Y plane (in a horizontal direction) relative to the subject 103. The moving mechanism 129 includes a motor, such as a stepping motor. The path of the movement of the supporting member 113 may be a two-dimensional spiral path or a linear path. The moving mechanism 129 may move the supporting member 113 in the Z-direction or rotate the supporting member 113 about a predetermined axis. As described above, the supporting member 113 includes the light emitting portion 125, so that light is radiated from below the subject 103.
Transducers 115
The transducers 115 may any other transducers that receive acoustic waves and convert them to electrical signals, such as piezoelectric devices using a piezoelectric phenomenon of lead zirconate titanate (PZT), transducers using interference of light, and capacitive transducers, such as capacitive micromachined ultrasonic transducers (CMUTs).

The plurality of transducers 115 are disposed, with the receiving surfaces along the spherical surface of the bowl-shaped portion. The pattern of disposition may be a pattern in which the plurality of transducers 115 are disposed in a three-dimensional spiral, as disclosed in International Publication No. WO/2010/030817. The disposition along the spherical surface allows a configuration in which directions of high receiving sensitivity of the transducers 115 point to specific areas.

Typically, the normal directions of the receiving surfaces (front surfaces) of the transducers 115 have the highest receiving sensitivity. Thus, disposing the transducers 115 along the spherical surface allows directions in which the receiving sensitivity of the transducers 115 is higher than a predetermined level to point to the vicinity of the center of curvature (a specific area) of the hemispherical bowl-shaped portion. In particular, the plurality of transducers 115 may be disposed so that directions of the highest sensitivity intersect in the vicinity of the curvature of the bowl-shaped portion.

In this embodiment, the resolution of an area to which directions in which the receiving sensitivity of the transducers 115 is higher than a predetermined level point can be enhanced. In this specification, such an area capable of high sensitivity reception is referred to as a high-sensitivity area, and the high-sensitivity area results in high resolution. The high-resolution area may have the highest resolution to half the highest resolution. Specifically, a diameter r in Eq. (1) is the diameter of the high-resolution area.

where R is an allowable resolution, $R_H$ is the highest resolution, $r_0$ is the diameter of a sphere on which the transducers 115 are disposed, and $\Phi_d$ is the diameter of each transducer 115.

In this embodiment, the disposition of the plurality of transducers 115 is given for illustration, and any other dispositions that allow a desired high-sensitivity area are possible. The disposition allowing the high-sensitivity area is a disposition that allows acoustic waves to be received with higher sensitivity than a disposition in which directions of the highest sensitivity of the transducers 115 are parallel to each other. The high-sensitivity area determined depending on the disposition of the plurality of transducers 115 is formed at an area in which the subject 103 is supposed to be placed for examination.

Specifically, the plurality of transducers 115 may be disposed so that the directions of the highest receiving sensitivity of at least two of the transducers 115 point to a specific area. In other words, the transducers 115 may be disposed so that the direction of the highest receiving sensitivity differs between part of the plurality of transducers 115 and another transducer 115 and that the directions of the highest receiving sensitivity point to a specific area. The directions of the highest receiving sensitivity of at least part of the plurality of transducers 115 may intersect one another.

Since the directions of the highest receiving sensitivity point to a specific area, acoustic waves generated from the specific area can be received with higher sensitivity than that when the directions of the highest receiving sensitivity of the transducers 115 are parallel. This can enhance the resolution of an image in the specific area as compared with that when the directions of the highest receiving sensitivity of the transducers 115 are parallel.

In other words, such a disposition allows the directional axes (axes along the directions of the highest receiving sensitivity) of at least part of the plurality of transducers 115 to be converged.

In other words, such a disposition is such that the receiving surfaces of the transducers 115 face the interior of the supporting member 113. That is to say, in the case where the transducers 115 are disposed on a supporting member having a curved surface, such as a spherical surface, the receiving surfaces of the transducers 115 are disposed along a surface adjacent to the center of curvature. In the case where the transducers 115 are disposed on a supporting member having a surface formed of a plurality of flat surfaces (angles that the flat surfaces form are obtuse angles), the receiving surfaces are disposed along the inner surface (a recess-side surface).

In this specification, "spherical surface" includes spherical surfaces other than the surface of a true sphere. In other words, "spherical surface" includes a spherical surface having an opening, such as a hemispherical surface. "Spherical surface" further includes a surface having surface irregularities to the extent that it is regarded as a spherical surface and the surface of an ellipsoid (a three-dimensional figure of an ellipse, whose surface is a quadratic surface) that can be regarded as a spherical surface.

Holding Member 109

The holding member 109 is disposed in an opening of a bed 105 on which an examinee 101 is laid face-down (prone position). A breast, which is the subject 103, is inserted through the opening and is held by the holding member 109. The holding member 109 holds the subject 103 so as to surround it. "Surround the subject" does not necessarily refer to surrounding all the directions of the subject 103. The holding member 109 may be a cup-shaped member, which allows the subject 103 to be supported from below in the direction of gravity.

The holding member 109 may be formed of a material having an acoustic impedance close to that of a human body. For example, the holding member 109 may have an acoustic impedance of 1.3 MRayls or higher and 2 MRayls or lower. The use of a material having such characteristics can reduce the reflection of acoustic waves at the interface between the subject 103 and the holding member 109. To reduce noise due to multiple reflection of acoustic waves, the holding member 109 may be thin. For example, the holding member 109 preferably has a thickness of 100 µm or less. Since light irradiates the subject 103 through the holding member 109, the holding member 109 may be formed of a material having high transmittance of light in a wavelength band used (preferably, 90% or higher). Specific examples of the material of the holding member 109 include polymethylpentene and polyethylene terephthalate.

The holding member 109 of this embodiment includes a marker 111 which is a light absorber that absorbs light to generate acoustic waves. The marker 111 has a higher light absorption coefficient than that of the cup-shaped portion of the holding member 109. In this embodiment, the use of received signals caused by the acoustic waves generated from the marker 111 can enhance the visibility of images (images displayed on a display unit 506) presented to the examiner or operator who is a user. An example of the marker 111 is a light absorber colored in black or gray. However, an excessive intensity of acoustic waves generated from the marker 111 can cause noise in obtaining characteristic information on the subject 103. Thus, the intensity of acoustic waves generated from the marker 111 may be equal to or one place less than the intensity of acoustic waves generated from the subject 103. The marker 111 preferably has an absorption coefficient of 0.05/mm or more and 1.0/mm or less considering that the absorption coefficient of hemoglobin, which is a typical substance that absorbs light in the subject 103, is between 0.3/mm and 0.9/mm.

The shape of the marker 111 may be selected depending on the use; for example, a dotted pattern, a line pattern, a matrix pattern, a radiating pattern, and a circular pattern.

Signal Collecting Unit 131

A signal collecting unit 131 is a circuit that collects time-series received signals output from the individual transducers 115 channel by channel. The signal collecting unit 131 may be a circuit generally referred to as a data acquisition system (DAS). Specifically, the signal collecting unit 131 includes an amplifier that amplifies received signals, an A-D converter that converts received analog signals to digital signals, and a memory that stores the received signals.

The signal processing unit 133 obtains distribution information including characteristic information on the interior of the subject 113 using received signals output from the signal collecting unit 131. Specifically, the signal processing unit 133 includes a reconstructing portion 433 that reconstructs images using the channel-by-channel received signals. Examples of a method for reconstructing images include known reconstructing methods, such as universal back projection (UBP) and filtered back projection (FBP) disclosed in U.S. Pat. No. 5,713,356. The image reconstruction allows the distribution of channel-by-channel time-series received signals on two- or three-dimensional coordinate axes (distribution corresponding to the space in the subject 103) to be generated. Examples of the reconstructing portion 433 include a CPU, a graphics processing unit (GPU), a field programmable gate array (FPGA) chip.

The signal processing unit 133 may include a signal storing portion 401 that stores received signals output from the signal collecting unit 131. Typical examples of the signal storing portion 401 are storage mediums, such as a ROM, a RAM, and a hard disk. The signal storing portion 401 may be either a single storage medium or a plurality of storage media.

Image Processing Unit 134

An image processing unit 134 generates image data to be displayed on the display unit 505. Specifically, the image processing unit 134 includes a display-image generating portion 503 that generates image data on the basis of the distribution information generated by the signal processing unit 133. The display-image generating portion 503 can perform the process of converting the intensity values at individual positions in the distribution to luminance values and the process of generating guide information to be displayed together with the distribution information. Examples of the display-image generating portion 503 include a CPU, a graphics processing unit (GPU), and a field programmable gate array (FPGA) chip.

The image processing unit 134 may include an image storing portion 501 that can store the distribution information output from the signal processing unit 133 and the image data generated by the display-image generating portion 503. Typical examples of the image storing portion 501 include storage mediums, such as a ROM, a RAM, and a hard disk. The signal storing portion may be either a single storage medium or a plurality of storage media.

The display unit 505 displays images on the basis of data output from the image processing unit 134. Examples of the display unit 505 include a liquid crystal display (LCD) a cathode ray tube (CRT), and an organic EL display. The display unit 505 may not be included in the subject-information processing apparatus but may be a separate unit connected to the subject-information acquisition apparatus. Examples in this embodiment will now be described in detail.

Example 1

Figure 2B:
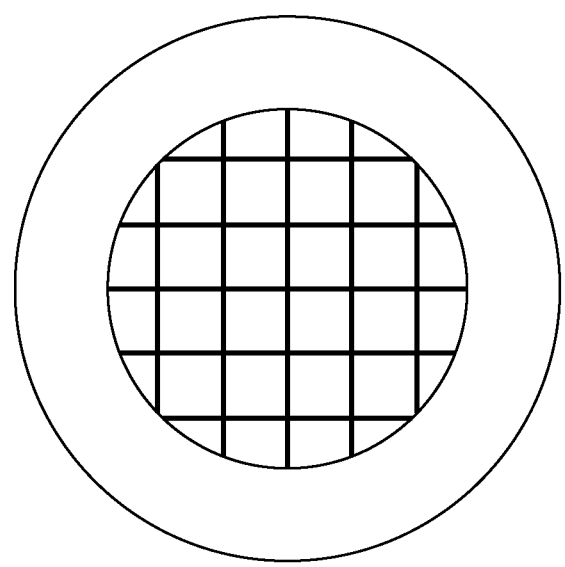
FIG. 2B is a schematic top view of the holding member.

In this example, a case in which the characteristic information on the subject 103 and the marker 111 are displayed will be described. The same subject-information acquisition apparatus as shown in FIG. 1 can be used. The configuration of the marker 111 is shown in FIGS. 2A and 2B. FIG. 2A is a schematic side view of the holding member 109; and FIG. 2B is a schematic top view thereof. The cup-shaped portion of the holding member 109 has a line marker 111a with a lattice pattern. The marker 111a generates acoustic waves when irradiated with pulsed light emitted from the light source 121. For example, the marker 111a is composed of lines made of acryl colored in gray with a width of about 0.5 mm.

In this example, when the subject 103 is irradiated with light while being held by the holding member 109, the signal processing unit 133 obtains received signals including a received signal caused by acoustic waves generated from the subject 103 and a received signal caused by acoustic waves generated from the marker 111a. The signal processing unit 133 reconstructs an image on the basis of the received signals including the two signal components to generate three-dimensional distribution information including the characteristic information on the interior of the subject 103 and the information based on the marker 111.

Since an image indicating such distribution information is displayed, the user can easily determine the position of the holding member 109. In other words, the user can determine the positions of the subject 103, the holding member 109, and the acoustic matching liquid 119 in the image indicating the distribution information with reference to the position of the marker 111a in the image.

Without the marker 111a, the position of the subject 103 in an image obtained by receiving acoustic waves cannot easily be viewed, because the holding member 109 and the acoustic matching liquid 119 are made of materials having acoustic impedances close to that of the subject 103.

In other words, providing the holding member 109 with the marker 111a, as in this example, can enhance the visibility of the position of the subject 103 in an image presented to the user.

Figure 3A:
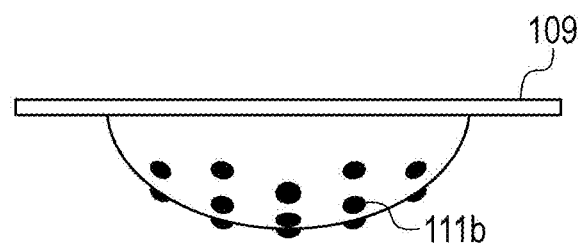
FIG. 3A is a schematic side view of another holding member.
Figure 3B:
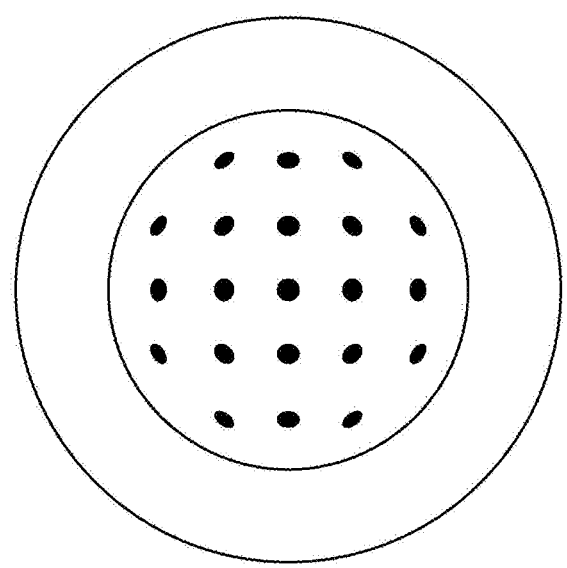
FIG. 3B is a schematic top view of the holding member.

The shape of the marker 111a shown in FIGS. 2A and 2B is illustrative only, and a dotted marker 111b shown in FIGS. 3A and 3B may be provided. FIG. 3A is a schematic side view of the holding member 109; and FIG. 3B is a schematic top view thereof. The marker 111 may be in a line pattern, a radiating pattern, or a circular pattern.

Example 2

In this example, not only an image generated on the basis of acoustic waves but also an image captured by an optical image-capturing unit are displayed.

Figure 4:
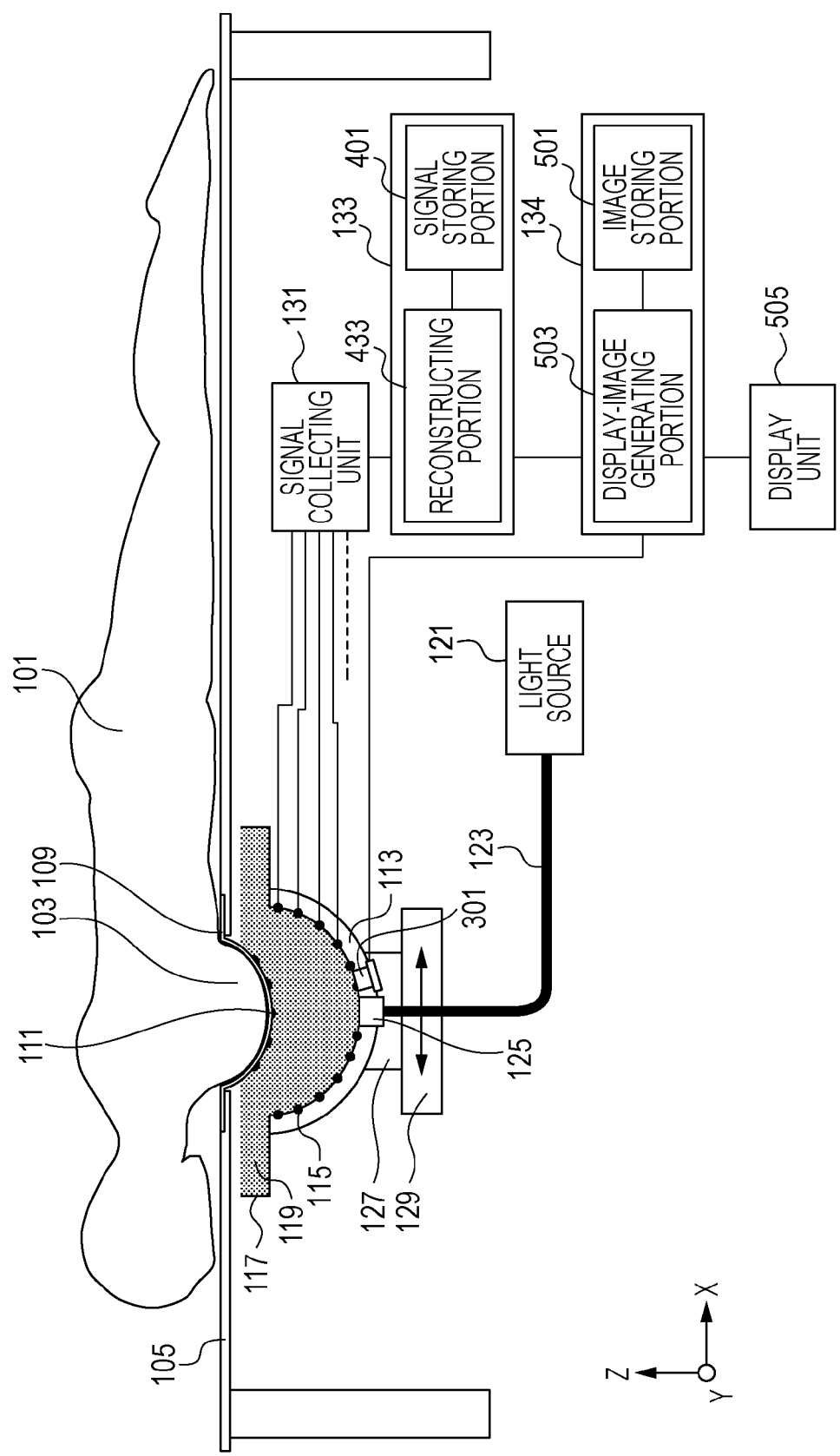
FIG. 4 is a schematic diagram of a subject-information acquisition apparatus of Example 2.

FIG. 4 is a schematic diagram of a subject-information acquisition apparatus of this example. In FIG. 4, the same components as those in FIG. 1 are denoted by the same reference signs, and descriptions thereof are omitted. The subject-information acquisition apparatus of this example includes an optical image-capturing unit 301 on the supporting member 113.

The optical image-capturing unit 301 is an image capturing apparatus that captures an optical image, that is, a camera. The optical image-capturing unit 301 includes an image capturing apparatus capable of capturing a three-dimensional optical image, that is, a time-of-flight (TOF) camera. The optical image-capturing unit 301 is disposed at a position at which images of the marker 111 (marker 111a) and the state (the external appearance) of the subject 103 held by the holding member 109 can be captured from the lower part of the internal space of the supporting member 113.

The image processing unit 134 displays an optical image (a photograph) captured by the optical image-capturing unit 301 and an image of distribution information input from the signal processing unit 133 on the same screen. This display method allows the user to compare the external appearance of the subject 103 and the distribution information on the interior of the subject 103 with each other, thus enhancing the user visibility.

Example 3

This example shows a case having a mode of generating an image in which information based on the marker 111 in the distribution information is reduced. In this example, the same subject-information acquisition apparatus as that in FIG. 1 or 4 can be used.

In this example, before examination, the signal storing portion 401 stores in advance received signals obtained by irradiating the holding member 109 with light in a state in which the holding member 109 does not hold the subject 103 (the subject 103 is not held in the holding member 109). In this case, the holding member 109 may be filled with, instead of the subject 103, a phantom member whose acoustic characteristics are similar to those of human bodies or an acoustic matching member whose acoustic impedance is close to that of the holding member 109, such as an acoustic medium, for example, water and oil. This is for the purpose of reducing multiple reflection of acoustic waves generated from the marker 111 in the holding member 109.

For examination, a received signal (a first received signal) in a state in which the holding member 109 holds the subject 103 (that is, the subject 103 is present in the holding member 109) is input to the signal processing unit 133, as in Examples 1 and 2. The signal processing unit 133 reads a received signal (a second received signal), stored in the signal storing portion 401, in a state in which the subject 103 is not held, and reduces signal components caused by the marker 111 using the first received signal and the second received signal. Typically, the signal processing unit 133 subtracts the second received signal from the first received signal.

This process allows received signals in which signal components coming from the marker 111 are reduced to be obtained. The signal components coming from the marker 111 may not necessarily be completely deleted but have only to be reduced. The reconstructing portion 433 reconstructs an image using the signal after the reducing process. This allows distribution information in which information based on the marker 111 is reduced (second distribution information) to be obtained. Not only the second distribution information but also distribution information including the characteristic information on the subject 103 and the marker 111 (first distribution information) may be generated by the method in Example 1.

FIGS. 5A and 5B schematically show the distribution information obtained in this example. FIG. 5A is a diagram in which the greatest value in the z-direction is projected to an X-Y plane in a three-dimensional image indicating the first distribution information; and FIG. 5B is a diagram in which the greatest value in the z-direction is projected to an X-Y plane in a three-dimensional image indicating the second distribution information. As shown in FIG. 5B, the image generated from the second distribution information does not show the marker 111. Displaying an image including no marker information allows the characteristic information on the interior of the subject 103 to be observed in detail.

The image processing unit 134 may execute at least one of a mode in which the first distribution information and the second distribution information are selected for display and a mode in which the first distribution information and the second distribution information are displayed side by side. The image processing unit 134 may execute a mode in which only one of images of the first distribution information and the second distribution information is displayed. Thus, the position of the subject 103 can be determined with an image including the marker 111 like the first distribution information, and the interior of the subject 103 can be viewed using an image in which marker information is reduced without the obstruction of marker information.

Example 4

An example including a mode in which an image in which information based on the marker 111 is reduced, as in Example 3, will be described. This example differs from Example 3 in a method for generating the second distribution information. The same subject-information acquisition apparatus as in FIG. 1 or 4 can be used.

Also in this example, before examination, a received signal (the second received signal) is obtained by irradiating the holding member 109 with light in a state in which the holding member 109 does not hold the subject 103 (the subject 103 is not held in the holding member 109). However, in this example, the reconstructing portion 433 generates distribution information (third distribution information) on a state in which the subject 103 is not present, that is, distribution information that does not include the characteristic information on the subject 103. The image storing portion 501 stores the third distribution information.

For examination, a received signal (the first received signal) in a state in which the holding member 109 holds the subject 103 (that is, the subject 103 is present in the holding member 109) is input to the signal processing unit 133, as in Examples 1 to 3. The reconstructing portion 433 reconstructs an image on the basis of the first received signal to generate the first distribution information.

The image processing unit 134 generates distribution information in which information based on the marker 111 is reduced using the first distribution information and the third distribution information. Typically, the image processing unit 134 subtracts the third distribution information from the first distribution information. This allows distribution information in which components based on the marker 111 are reduced (the second distribution information) to be obtained. Also in this example, the signal components coming from the marker 111 may not necessarily be completely deleted but have only to be reduced.

Also in this example, the image processing unit 134 may execute at least one of a mode in which the first distribution information and the second distribution information are selected for display and a mode in which the first distribution information and the second distribution information are displayed side by side. The image processing unit 134 may execute a mode in which only one of images of the first distribution information and the second distribution information is displayed. Thus, the position of the subject 103 can be determined with an image including the marker 111 like the first distribution information, and the interior of the subject 103 can be viewed using an image in which marker information is reduced without the obstruction of marker information. In this example, since the third distribution information can also be obtained, the third distribution information may be displayed.

In this example, the third distribution information may not necessarily be generated before examination. If the second received signal is stored in the signal storing portion 401, the third distribution information can be generated during or after the generation of the first distribution information.

Example 5

This example shows a case in which guide information indicating the position of the holding member 109 or the position of the subject 103 is generated for display. The same subject-information acquisition apparatus as that of FIG. 1 or 4 can be used.

In this example, the image processing unit 134 generates guide information indicating the position of the holding member 109 or the position of the subject 103 using received signals caused by the marker 111. The generated guide information is superimposed on the first distribution information or the second distribution information obtained by the processes described in Examples 1 to 4 for display.

Figure 6A:
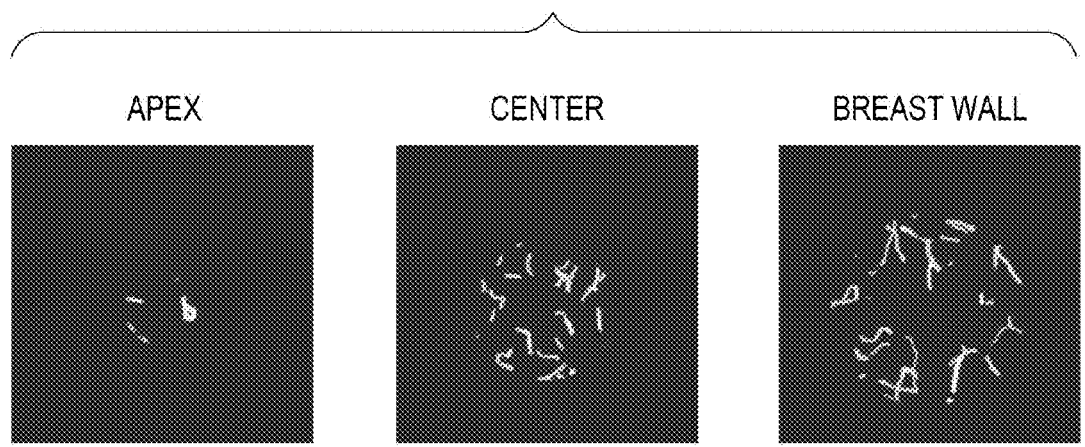
FIG. 6A schematically shows tomograms of second distribution information in which no guide is displayed.
Figure 6B:
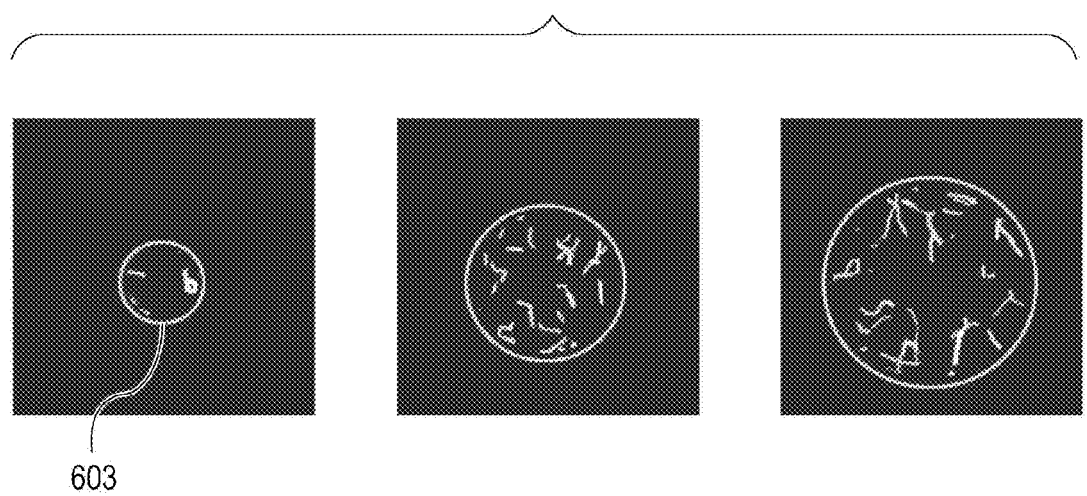
FIG. 6B schematically shows tomograms of second distribution information in which a guide is superimposed.

The details will be described with reference to FIGS. 6A and 6B. FIGS. 6A and 6B are schematic diagrams of images of distribution information indicating tomograms in X-Y section. FIG. 6A schematically shows tomograms of second distribution information without a guide; and FIG. 6B schematically shows tomograms of second distribution information in which a guide is superimposed. FIG. 6B shows a circle 603 indicating the contour of the holding member 109 serving as a guide indicating the position of the holding member 109.

In FIGS. 6A and 6B, the left diagram shows a tomogram of the apex (lower end) of the holding member 109, the central diagram shows a tomogram of the central portion of the holding member 109, and the right diagram show a tomogram of a breast-wall-side portion.

Even if information based on the marker 111 is not displayed, the subject 103 can be located by displaying guide information indicating the position of the holding member 109. Even if information based on the marker 111, like the first distribution information, is displayed, the marker 111 is sometimes not displayed depending on the slice position of the tomogram. Even in such a case, the subject 103 can be located by additionally displaying the guide information.

The guide information can be generated using received signals containing signal components coming from the marker 111. The guide information may be generated not directly from received signals but from the first distribution information or the third distribution information.

The guide may not necessarily have a circular shape indicating the contour, as shown in FIG. 6B. An area in the holding member 109 and an area outside the holding member 109 may be distinguished by using different colors; any other guides that allow the user to locate the subject 103 are possible.

Example 6

This example shows a marker that allows the orientation of an image to be determined. The same subject-information acquisition apparatus as that in FIG. 1 or 4 may be used.

Figure 7A:
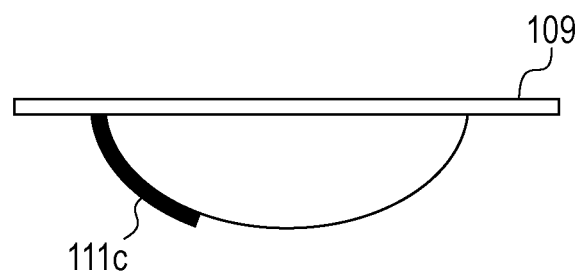
FIG. 7A is a schematic side view of another holding member.
Figure 7B:
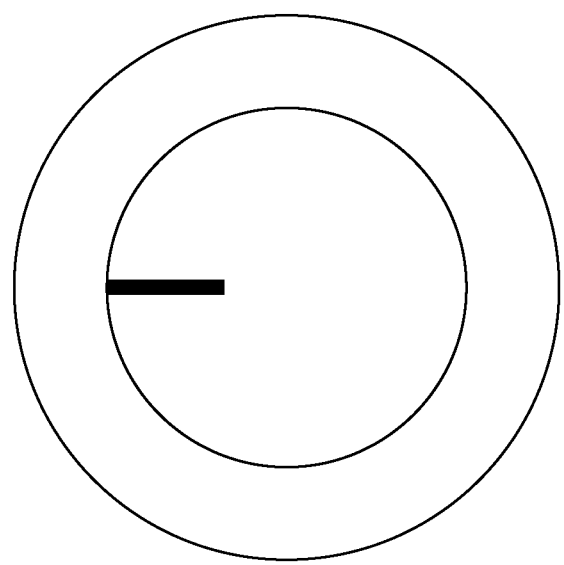
FIG. 7B is a schematic top view of the holding member.

FIGS. 7A and 7B are schematic diagrams of a marker 111c of this example. FIG. 7A is a schematic side view of the holding member 109; and FIG. 7B is a schematic top view thereof. In FIGS. 7A and 7B, the marker 111c is at a position near the head of the examinee 101 and has a line shape in top view in the axial direction of the body (a direction extending from the head to the feet).

This marker 111c is effective when the holding member 109 has a cup-shaped portion having a spherical surface. With an axisymmetric form, like a hemispherical cup, if a three-dimensional image indicating distribution information is rotationally displayed, the orientations of the three-dimensional images of the subject 103 displayed at individual timings may not easily be determined intuitively. For example, it is difficult to determine whether the images are viewed from the head side or from the right.

However, the use of the marker 111c asymmetric to the central axis (an axis passing through the center of curvature) of the holding member 109 makes it easy to determine which orientations the images are viewed from, because the view of the marker 111c in the three-dimensional image varies with orientation.

Second Embodiment

Next, a second embodiment will be described. In this embodiment, an example of setting a sound velocity in an acoustic medium (the propagation velocity of acoustic waves) between the transducers 115 and the holding member 109 using a marker will be described.

Figure 8:
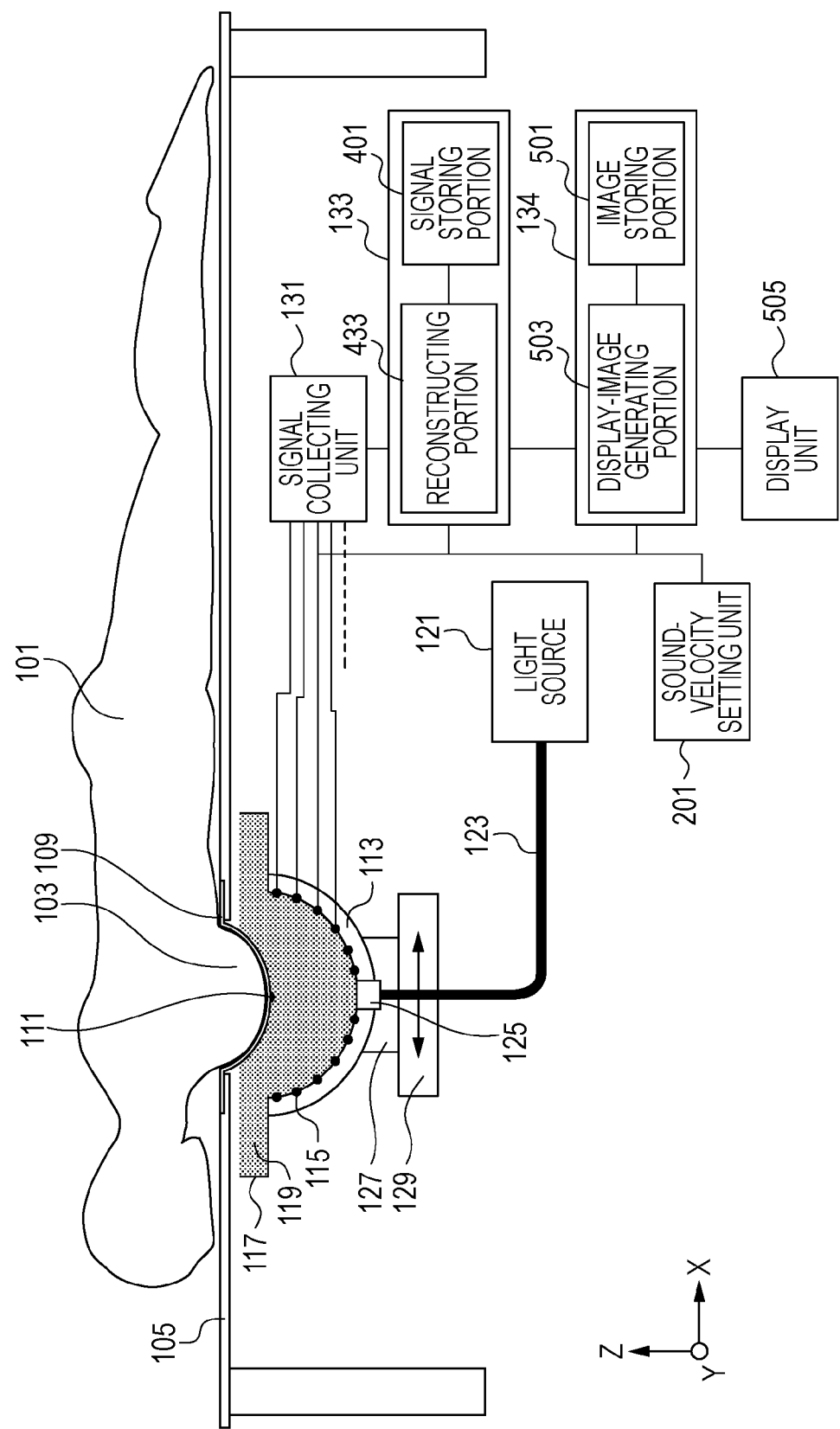
FIG. 8 is a schematic diagram of a subject-information acquisition apparatus of a second embodiment.

FIG. 8 is a schematic diagram of a subject-information acquisition apparatus of this embodiment. The apparatus in FIG. 8 includes a sound-velocity setting unit 201. Like components described in the first embodiment are denoted by the same reference signs, and descriptions thereof will be omitted.

In this embodiment, the sound-velocity setting unit 201 sets a sound velocity using received signals caused by the acoustic waves generated from the marker 111. The details will be described in the following examples. Also in this embodiment, information on the marker 111 and the guide may be displayed on an image to be presented to the user by application of the first embodiment. In other words, Examples 1 to 6 may be combined to the second embodiment.

Example 7

Figure 9A:
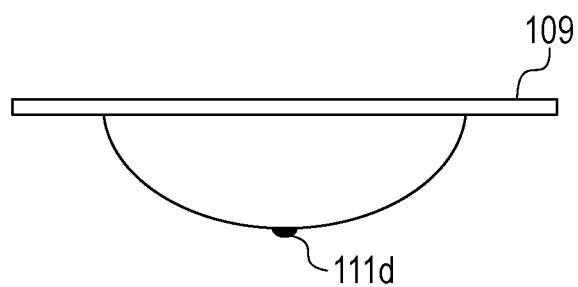
FIG. 9A is a schematic side view of another holding member.
Figure 9B:
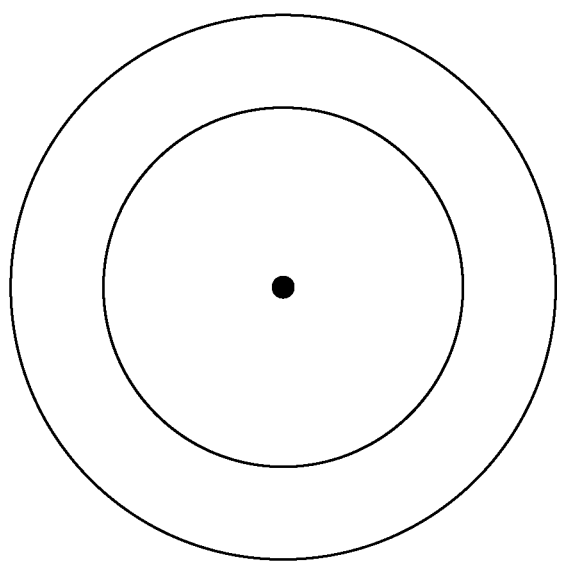
FIG. 9B is a schematic top view of the holding member.

In this example, a configuration in which the user can set a sound velocity on the basis of an image of the marker 111 will be described. FIGS. 9A and 9B are schematic diagrams showing the configuration of a marker 111d of the holding member 109. FIG. 9A is a schematic side view of the holding member 109, and FIG. 9B is a schematic top view thereof.

In FIGS. 9A and 9B, a point-like marker 111d is provided at the apex (a lower end in the direction of gravity) of the cup-shaped portion of the holding member 109. The marker 111d generates acoustic waves when irradiated with pulsed light emitted from the light source 121. For example, the marker 111d is a point made of acryl colored in gray with a diameter of about 0.5 mm. The marker 111 may have any shape, as described in the first embodiment.

In this example, when the subject 103 is irradiated with light while being held by the holding member 109, the signal processing unit 133 obtains received signals including received signals caused by acoustic waves generated from the subject 103 and received signals caused by acoustic waves generated from the marker 111d.

The importance of setting the sound velocity will now be described. The sound velocity in the acoustic matching liquid 119 changes with temperature. If the temperature of the acoustic matching liquid 119 changes during examination, a deviation of an actual sound velocity from a set sound velocity may degrade the resolution of the image. This will be described with reference to FIGS. 10A and 10B.

Figure 10A:
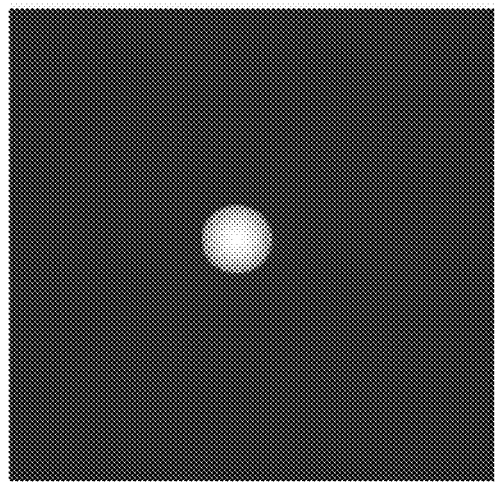
FIG. 10A is a schematic diagram of a two-dimensional image obtained when a sound velocity is properly set.
Figure 10B:
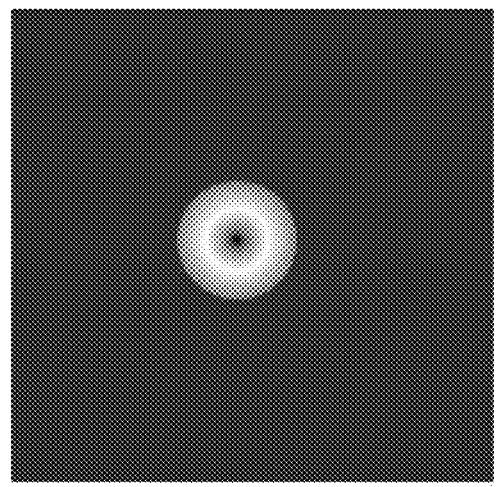
FIG. 10B is a schematic diagram of a two-dimensional image obtained when a sound velocity different from an actual sound velocity is set.

FIG. 10A is a schematic diagram of a two-dimensional image of distribution information taken along an X-Y section including the marker 111d in the case where the sound velocity in the acoustic matching liquid 119 is properly set. FIG. 10B is a schematic diagram of a two-dimensional image of distribution information taken along an X-Y section including the marker 111d in the case where a sound velocity different from an actual sound velocity is set. If a proper sound velocity is set, information on the marker 111d is resolved as a point; if an improper sound velocity is set, the information is resolved as a ring, thus degrading the resolution.

In this example, the sound-velocity setting unit 201 is configured to be capable to set an optimum sound velocity for the acoustic matching liquid 119 in accordance with an instruction of the user so as to form a high-resolution image of the marker 111d. Specifically, the signal processing unit 133 generates distribution information for prepared different sound velocities in reconstructing an image on the basis of obtained received signals. In other words, the signal processing unit 133 generates a plurality of items of distribution information. The image processing unit 134 displays the plurality of items of distribution information on the display unit 505.

The user determines an image in which the marker 111d has the highest contrast while viewing the images of the plurality of items of distribution information and instructs the sound-velocity setting unit 201 to set information on the sound velocity via an input unit (not shown). The sound-velocity setting unit 201 sets the information on the sound velocity as an optimum sound velocity to the signal processing unit 133 in response to the instruction from the user.

The signal processing unit 133 generates distribution information again using the set optimum sound velocity. Alternatively, the signal processing unit 133 may output distribution information generated using the same sound velocity, which has already been obtained, as the optimum sound velocity to the image processing unit 134 again.

In the case where acoustic waves are to be obtained at a plurality of detection positions while the supporting member 113 is moving relative to the subject 103, an optimum sound velocity may set on the basis of a received signal obtained at one detection position (a first detection position), and the optimum sound velocity may be used at another detection position (a second detection position). In other words, the signal processing unit 133 may perform image reconstruction using a received signal obtained at the second detection position and the optimum sound velocity.

In this example, since a sound velocity that the user sets on the basis of an image based on the marker 111d can be used, distribution information with enhanced resolution can be finally obtained. The marker 111d of this example is disposed at the apex of the holding member 109. This is for the purpose of preventing signal components caused by acoustic waves generated at the marker 111d from being added to distribution information as artifacts. Disposing the marker 111d at such a position allows the acoustic waves generated from the marker 111d to reach most of the plurality of transducers 115 earlier than acoustic waves generated from the subject 103. This can decrease the proportion of superposed acoustic waves generated from the marker 111d.

If an influence of the artifacts due to the acoustic waves generated from the marker 111d on the image is small, the marker 111d may be disposed at a position other than the apex of the cup-shaped portion. When the supporting member 113 is moved relative to the subject 103, the positional relationship between the apex of the cup-shaped portion and the plurality of transducers 115 also changes. In such a case, the marker 111d may be provided at a position closest to the initial position of the moving pattern of the supporting member 113.

In Example 7, received signals are obtained in a state in which the subject 103 is held by the holding member 109 (during examination), and the sound velocity is set on the basis of distribution information generated using the received signals; this example is not limited thereto. The sound velocity may be set on the basis of distribution information generated using received signals obtained in a state in which the subject 103 is not held by the holding member 109, such as directly before examination.

Example 8

This example shows a case in which the sound-velocity setting unit 201 determines a sound velocity. In this example, the same subject-information acquisition apparatus as that in FIG. 8 can be used. This example differs from Example 7 in which the sound-velocity setting unit 201 has the function of determining an optimum sound velocity. An example in which the marker 111d as in FIGS. 9A and 9B is used will be described. FIG. 11 is a flowchart for explaining the processes of the sound-velocity setting unit 201 and the signal processing unit 133 of this example.

In this example, first in S101, the signal processing unit 133 obtains received signals obtained in a state in which the subject 103 is held by the holding member 109.

In S102, the signal processing unit 133 generates distribution information at a plurality of different sound velocities prepared in advance. In other words, the signal processing unit 133 generates a plurality of items of distribution information.

In S103, the sound-velocity setting unit 201 determines a sound velocity in the acoustic matching liquid 119 at which the contrast of the marker 111d is the highest from the plurality items of distribution information. For example, the sound-velocity setting unit 201 determines distribution information in which the half-value width of an X-axial intensity distribution in the area of the marker 111d is the smallest as distribution information in which the marker 111d has the highest contrast among the plurality of items of distribution information. A sound velocity used in generating the selected distribution information may be determined as an optimum sound velocity.

In S104, the information on the optimum sound velocity determined by the sound-velocity setting unit 201 is set to the signal processing unit 133, and the signal processing unit 133 generates distribution information using the optimum sound velocity and the received signal. Alternatively, distribution information generated using the same sound velocity as the optimum sound velocity, obtained in S102, may be output to the image processing unit 134 again.

In this example, since a sound velocity is determined without the user inputting an instruction on the sound velocity, as in Example 7, distribution information with high resolution can be obtained without a load on the user.

In obtaining acoustic waves at a plurality of detection positions while the supporting member 113 is moving relative to the subject 103, an optimum sound velocity may be determined in the above flow on the basis of a received signal obtained at one detection position (the first detection position), and the optimum sound velocity may be used also at another detection position (the second detection position). In other words, the signal processing unit 133 may perform image reconstruction using the optimum sound velocity obtained from the distribution information at the first detection position and the received signal obtained at the second detection position.

In Example 8, received signals are obtained in a state in which the subject 103 is held by the holding member 109 (during examination), and the sound velocity is set on the basis of distribution information generated using the received signals; this example is not limited thereto. The sound velocity may be set on the basis of distribution information generated using received signals obtained in a state in which the subject 103 is not held by the holding member 109, such as directly before examination.

Modification of Example 8

The sound-velocity setting unit 201 may determine a sound velocity not from distribution information, as in FIG. 11, but directly from received signals. In other words, the sound-velocity setting unit 201 may determine a sound velocity from time-axis changes in the intensity of received signals output from the signal collecting unit 131.

Specifically, the sound-velocity setting unit 201 uses channel-by-channel time-series received signals from the signal collecting unit 131 and information on light irradiation timing from a photodetector (not shown). The distance between the marker 111d and the transducers 115 is a known distance. Thus, the sound-velocity setting unit 201 can calculate the time taken for acoustic waves from the marker 111d to reach the transducers 115 by regarding the light irradiation timing as the timing of generation of acoustic waves from the marker 111d and by regarding a received signal that reaches first as a component caused by the acoustic waves generated from the marker 111d. After the time taken for arrival has been determined, the sound-velocity setting unit 201 can determine the sound velocity in the acoustic matching liquid 119 from the time taken for arrival and the distance between the marker 111d and the transducers 115.

The subsequent process is the same as S104 in FIG. 11. This method of determining the sound velocity allows the sound velocity to be determined without the need for the user to enter an instruction on the sound velocity, thus providing high-resolution distribution information without a load on the user.

Third Embodiment

Embodiments of the present invention can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-227235 filed Oct. 31, 2013 which is hereby incorporated by reference herein in its entirety.

What is claimed is:

1. A subject-information acquisition apparatus comprising:
   a light source;
   a holding member configured to hold a subject and including a marker that absorbs light and generates an acoustic wave;
   at least one transducer configured to receive an acoustic wave generated by irradiating the subject with light from the light source;
   a signal processing unit configured to obtain a photoacoustic image using a first received signal and a second received signal output from the transducer; and
   an image processing unit configured to cause a display unit to display the photoacoustic image with guide information indicating a shape of the holding member;
   wherein, in a state in which the subject is held by the holding member, the light source is adapted to irradiate the subject and the marker and the at least one transducer receives an acoustic wave generated by irradiating the subject and the marker and outputs the first received signal,
   wherein, in a state in which the subject is not held by the holding member, the light source irradiates the marker and the at least one transducer receives an acoustic wave generated by irradiating the marker and outputs the second received signal,
   wherein the signal processing unit is configured to generate the photoacoustic image on characteristic information on the interior of the subject on the basis of the first received signal and the second received signal, in a manner that information based on the marker in the photoacoustic image is reduced, and
   wherein the image processing unit is configured to generate the guide information indicating the shape of the holding member using a portion of the first received signal or the second received signal due to the marker.

2. The subject-information acquisition apparatus according to claim 1, wherein the signal processing unit is configured to obtain a first photoacoustic image on the basis of the first received signal, and obtain the photoacoustic image as a second photoacoustic image on the basis of the first and second received signals, and
   wherein at least one of the first photoacoustic image and the second photoacoustic image are selectively displayed and the first photoacoustic image and the second photoacoustic image are displayed side by side.

3. The subject-information acquisition apparatus according to claim 1, wherein the second received signal is obtained when an audio matching member is held in the holding member.

4. The subject-information acquisition apparatus according to claim 1, further comprising:
   an optical image-capturing unit disposed at a position where an optical image of a state in which the subject is held by the holding member can be captured,
   wherein, the optical image captured by the optical image-capturing unit is displayed.

5. The subject-information acquisition apparatus according to claim 1, further comprising:
   a sound-velocity setting unit configured to set a sound velocity in propagation pass of the acoustic wave generated from the marker on the basis of the portion of the first received signal or the second received signal due to the marker,
   wherein the signal processing unit is configured to generate the photoacoustic image using information on the sound velocity set by the sound-velocity setting unit.

6. The subject-information acquisition apparatus according to claim 1, further comprising:
   a supporting member,
   wherein the at least one transducer includes a plurality of transducers,
   wherein the supporting member supports the plurality of transducers, and
   wherein the plurality of transducers is disposed on the supporting member so that the direction of the highest receiving sensitivity differs between part of the plurality of transducers and another transducer of the plurality of transducers.

7. The subject-information acquisition apparatus according to claim 1, wherein the holding member is a cup-shaped member.

8. The subject-information acquisition apparatus according to claim 1, wherein the marker has a line shape.

9. The subject-information acquisition apparatus according to claim 1, wherein the marker has a dot shape.

10. A method for displaying an image generated by a subject-information acquisition apparatus on a display unit, the subject-information acquisition apparatus comprising:
   a light source;
   a holding member configured to hold a subject and including a marker that absorbs light and generates an acoustic wave;
   at least one transducer configured to receive an acoustic wave generated by irradiating the subject with light from the light source;
   a signal processing unit configured to obtain a photoacoustic image using a first received signal and a second received signal output from the transducer; and
   an image processing unit configured to cause a display unit to display the photoacoustic image with guide information indicating a shade of the holding member;
   the method comprising the steps of:
   in a state in which the subject is held by the holding member, irradiating the subject and the marker with the light and the at least one transducer receiving an acoustic wave generated by irradiating the subject and the marker and and outputting the first received signal,
   in a state in which the subject is not held by the holding member, irradiating the marker with the light and the at least one transducer receiving an acoustic wave generated by irradiating the marker and outputting the second received signal,
   generating the photoacoustic image on characteristic information on the interior of the subject on the basis of the first received signal and the second received signal, in a manner that information based on the marker in the photoacoustic image is reduced; and
   generating the guide information indicating the shape of the holding member using a portion of the first received signal or the second received signal due to the marker.

11. The display method according to claim 10, further comprising the steps of:
   obtaining a first photoacoustic image generated on the basis of the first received signal, and obtaining the photoacoustic image as a second photoacoustic image generated on the basis of the first and second received signals, and
   selectively displaying at least one of the first photoacoustic image and the second photoacoustic image or displaying the first photoacoustic image and the second photoacoustic image side by side.

12. The display method according to claim 10, further comprising the steps of:
   capturing an optical image of a state in which the subject is held by the holding member, and displaying the captured optical image.

13. The display method according to claim 10, further comprising the steps of:
   setting a sound velocity in propagation pass of the acoustic wave generated from the marker on a basis of the portion of the first received signal or the second received signal due to the marker,
   wherein the photoacoustic image is generated using information on the set sound velocity.

* * * * *